United States Patent
Atladottir et al.

(10) Patent No.: US 8,728,149 B2
(45) Date of Patent: *May 20, 2014

(54) ASSEMBLY FOR MAKING A POLYMERIC MEDICAL DEVICE

(75) Inventors: Svava Maria Atladottir, Burlingame, CA (US); David C. Gale, San Jose, CA (US); Klaus Kleine, Los Gatos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 75 days.

This patent is subject to a terminal disclaimer.

(21) Appl. No.: 13/244,225

(22) Filed: Sep. 23, 2011

(65) Prior Publication Data

US 2012/0013061 A1    Jan. 19, 2012

Related U.S. Application Data

(60) Continuation of application No. 12/579,359, filed on Oct. 14, 2009, now Pat. No. 8,066,762, which is a division of application No. 11/157,145, filed on Jun. 20, 2005, now Pat. No. 7,622,070.

(51) Int. Cl.
*A61F 2/06* (2013.01)
*B23Q 1/00* (2006.01)
*B29C 35/08* (2006.01)

(52) U.S. Cl.
USPC .............................. 623/1.38; 269/47; 264/400

(58) Field of Classification Search
CPC ........... A61L 31/16; A61L 31/14; A61F 2/91; B23K 26/4065
USPC ........... 623/1.38–1.54, 1.23, 1.15, 1.13, 1.16, 623/1.36; 264/400, 482; 219/121.67; 269/47

See application file for complete search history.

(56) References Cited

U.S. PATENT DOCUMENTS

| | | | | |
|---|---|---|---|---|
| 3,882,816 | A | * | 5/1975 | Rooz et al. ..................... 118/57 |
| 3,995,075 | A | * | 11/1976 | Cernauskas et al. .......... 427/236 |
| 4,082,212 | A | * | 4/1978 | Headrick et al. .............. 228/147 |
| 4,110,497 | A | * | 8/1978 | Hoel .............................. 428/190 |
| 4,321,711 | A | * | 3/1982 | Mano ........................... 623/1.43 |
| 4,343,931 | A | * | 8/1982 | Barrows ....................... 528/291 |
| 4,529,792 | A | * | 7/1985 | Barrows ....................... 528/291 |
| 4,674,506 | A | * | 6/1987 | Alcond ......................... 606/153 |
| 4,738,740 | A | * | 4/1988 | Pinchuk et al. ............... 156/167 |
| 4,740,207 | A | * | 4/1988 | Kreamer ...................... 623/1.15 |
| 4,743,252 | A | * | 5/1988 | Martin et al. ................. 623/1.44 |
| 4,762,128 | A | * | 8/1988 | Rosenbluth ................... 606/192 |

(Continued)

FOREIGN PATENT DOCUMENTS

DE    199 01 530    7/2000

OTHER PUBLICATIONS

International Search Report for PCT/US2006/020883 filed May 26, 2006, mailed Sep. 11, 2007, 12 pgs.

*Primary Examiner* — Alvin J. Stewart
(74) *Attorney, Agent, or Firm* — Squire Sanders (US) LLP

(57) ABSTRACT

A polymeric tube is positioned on a polymeric mandrel and then laser cut to form an implantable medical device, such as a stent. The assembly and method reduces contamination of the inner surface of the stent, which would be caused if conventional glass or metal mandrels are used, while simultaneously reducing damage to the inner surface of the stent due to the shielding effect of the polymeric mandrel.

20 Claims, 4 Drawing Sheets

(56) References Cited

U.S. PATENT DOCUMENTS

| | | | |
|---|---|---|---|
| 4,816,339 A * | 3/1989 | Tu et al. | 428/421 |
| 4,955,899 A * | 9/1990 | Della Corna et al. | 623/1.46 |
| 5,100,429 A | 3/1992 | Sinofsky et al. | |
| 5,342,348 A | 8/1994 | Kaplan | |
| 5,421,955 A | 6/1995 | Lau et al. | |
| 5,441,515 A | 8/1995 | Khosravi et al. | |
| 5,605,696 A | 2/1997 | Eury et al. | |
| 5,629,077 A | 5/1997 | Turnlund et al. | |
| 5,632,840 A | 5/1997 | Campbell | |
| 5,674,242 A | 10/1997 | Phan et al. | |
| 5,679,400 A | 10/1997 | Tuch | |
| 5,693,085 A | 12/1997 | Buirge et al. | |
| 5,700,285 A * | 12/1997 | Myers et al. | 623/1.13 |
| 5,713,949 A | 2/1998 | Jayaraman | |
| 5,759,192 A * | 6/1998 | Saunders | 606/194 |
| 5,780,807 A | 7/1998 | Saunders | |
| 5,788,626 A * | 8/1998 | Thompson | 623/1.15 |
| 5,788,979 A * | 8/1998 | Alt et al. | 424/426 |
| 5,824,048 A | 10/1998 | Tuch | |
| 5,843,172 A | 12/1998 | Yan | |
| 5,861,714 A * | 1/1999 | Wei et al. | 313/625 |
| 5,868,781 A | 2/1999 | Killion | |
| 5,897,911 A | 4/1999 | Loeffler | |
| 5,906,759 A | 5/1999 | Richter | |
| 5,908,410 A * | 6/1999 | Weber et al. | 604/523 |
| 5,922,005 A | 7/1999 | Richter et al. | |
| 5,935,135 A * | 8/1999 | Bramfitt et al. | 623/1.11 |
| 5,935,506 A * | 8/1999 | Schmitz et al. | 264/400 |
| 5,972,027 A | 10/1999 | Johnson | |
| 6,004,348 A | 12/1999 | Banas et al. | |
| 6,013,099 A | 1/2000 | Dinh et al. | |
| 6,066,156 A * | 5/2000 | Yan | 606/192 |
| 6,068,202 A * | 5/2000 | Hynes et al. | 239/290 |
| 6,139,573 A * | 10/2000 | Sogard et al. | 623/1.13 |
| 6,143,370 A * | 11/2000 | Panagiotou et al. | 427/422 |
| 6,160,240 A * | 12/2000 | Momma et al. | 219/121.85 |
| 6,165,211 A * | 12/2000 | Thompson | 623/1.13 |
| 6,245,076 B1 * | 6/2001 | Yan | 606/108 |
| 6,245,099 B1 * | 6/2001 | Edwin et al. | 623/1.13 |
| 6,273,878 B1 * | 8/2001 | Muni | 604/265 |
| 6,305,436 B1 * | 10/2001 | Andersen et al. | 140/107 |
| 6,423,092 B2 | 7/2002 | Datta et al. | |
| 6,436,056 B1 * | 8/2002 | Wang et al. | 600/585 |
| 6,485,512 B1 | 11/2002 | Cheng | |
| 6,492,615 B1 | 12/2002 | Flanagan | |
| 6,506,437 B1 | 1/2003 | Harish et al. | |
| 6,521,284 B1 * | 2/2003 | Parsons et al. | 427/2.24 |
| 6,530,950 B1 | 3/2003 | Alvarado et al. | |
| 6,565,599 B1 * | 5/2003 | Hong et al. | 623/1.15 |
| 6,565,659 B1 * | 5/2003 | Pacetti et al. | 118/500 |
| 6,572,651 B1 | 6/2003 | De Scheerder et al. | |
| 6,585,755 B2 | 7/2003 | Jackson et al. | |
| 6,585,765 B1 * | 7/2003 | Hossainy et al. | 623/1.45 |
| 6,626,939 B1 * | 9/2003 | Burnside et al. | 623/1.38 |
| 6,663,662 B2 | 12/2003 | Pacetti et al. | |
| 6,666,880 B1 * | 12/2003 | Chiu et al. | 623/1.11 |
| 6,673,154 B1 * | 1/2004 | Pacetti et al. | 118/500 |
| 6,682,771 B2 * | 1/2004 | Zhong et al. | 427/2.24 |
| 6,695,920 B1 | 2/2004 | Pacetti et al. | |
| 6,716,444 B1 | 4/2004 | Castro et al. | |
| 6,719,934 B2 * | 4/2004 | Stinson | 264/40.1 |
| 6,726,829 B2 * | 4/2004 | Trozera | 205/655 |
| 6,753,071 B1 | 6/2004 | Pacetti | |
| 6,764,505 B1 | 7/2004 | Hossainy et al. | |
| 6,790,226 B2 | 9/2004 | Edwin et al. | |
| 6,790,228 B2 | 9/2004 | Hossainy et al. | |
| 6,818,063 B1 * | 11/2004 | Kerrigan | 118/500 |
| 6,866,805 B2 | 3/2005 | Hong et al. | |
| 6,887,510 B2 * | 5/2005 | Villareal | 427/2.24 |
| 6,916,409 B1 | 7/2005 | Callol et al. | |
| 6,920,677 B2 * | 7/2005 | Dolan et al. | 29/557 |
| 6,955,723 B2 * | 10/2005 | Pacetti et al. | 118/500 |
| 6,969,480 B2 | 11/2005 | Dalton et al. | |
| 7,060,150 B2 | 6/2006 | Banes et al. | |
| 7,077,859 B2 * | 7/2006 | Sirhan et al. | 623/1.15 |
| 7,083,642 B2 * | 8/2006 | Sirhan et al. | 623/1.42 |
| 7,112,298 B2 | 9/2006 | Kampa et al. | |
| 7,455,687 B2 * | 11/2008 | Saunders et al. | 623/1.16 |
| 7,473,265 B2 | 1/2009 | Linder et al. | |
| 7,485,141 B2 | 2/2009 | Majercak et al. | |
| 7,488,444 B2 * | 2/2009 | Furst et al. | 420/429 |
| 7,622,070 B2 * | 11/2009 | Atladottir et al. | 264/400 |
| 7,704,545 B2 | 4/2010 | Kantor | |
| 7,758,629 B2 * | 7/2010 | Holloway et al. | 623/1.16 |
| 7,771,581 B2 | 8/2010 | Callol et al. | |
| 7,897,168 B2 * | 3/2011 | Chen et al. | 424/426 |
| 7,910,038 B2 * | 3/2011 | Kia et al. | 264/313 |
| 8,066,762 B2 * | 11/2011 | Atladottir et al. | 623/1.42 |
| 8,206,635 B2 * | 6/2012 | Ramzipoor et al. | 264/294 |
| 8,250,754 B2 * | 8/2012 | Seifert | 29/883 |
| 8,373,090 B2 * | 2/2013 | Gale et al. | 219/121.67 |
| 2002/0038767 A1 * | 4/2002 | Trozera | 205/667 |
| 2002/0065553 A1 | 5/2002 | Weber | |
| 2002/0082679 A1 | 6/2002 | Sirhan et al. | |
| 2002/0138133 A1 | 9/2002 | Lenz et al. | |
| 2002/0165601 A1 * | 11/2002 | Clerc | 623/1.13 |
| 2002/0188037 A1 * | 12/2002 | Chudzik et al. | 523/112 |
| 2003/0033007 A1 * | 2/2003 | Sirhan et al. | 623/1.42 |
| 2003/0040790 A1 | 2/2003 | Furst | |
| 2003/0060877 A1 | 3/2003 | Falotico et al. | |
| 2003/0068355 A1 * | 4/2003 | Shanley et al. | 424/426 |
| 2003/0069629 A1 | 4/2003 | Jadhav et al. | |
| 2003/0072868 A1 | 4/2003 | Harish et al. | |
| 2003/0083646 A1 * | 5/2003 | Sirhan et al. | 604/891.1 |
| 2003/0088307 A1 | 5/2003 | Shulze et al. | |
| 2003/0104028 A1 * | 6/2003 | Hossainy et al. | 424/424 |
| 2003/0113439 A1 * | 6/2003 | Pacetti et al. | 427/2.24 |
| 2003/0114917 A1 * | 6/2003 | Holloway et al. | 623/1.13 |
| 2003/0118649 A1 * | 6/2003 | Gao et al. | 424/471 |
| 2003/0158517 A1 * | 8/2003 | Kokish | 604/103.01 |
| 2003/0171053 A1 | 9/2003 | Sanders | 442/340 |
| 2003/0190406 A1 * | 10/2003 | Hossainy et al. | 427/2.25 |
| 2003/0211230 A1 * | 11/2003 | Pacetti et al. | 427/2.24 |
| 2003/0215564 A1 * | 11/2003 | Heller et al. | 427/2.25 |
| 2003/0226833 A1 | 12/2003 | Shapovalov et al. | |
| 2003/0236563 A1 * | 12/2003 | Fifer | 623/1.11 |
| 2004/0018296 A1 * | 1/2004 | Castro et al. | 427/2.25 |
| 2004/0029952 A1 | 2/2004 | Chen et al. | |
| 2004/0034408 A1 | 2/2004 | Majercak et al. | |
| 2004/0047978 A1 * | 3/2004 | Hossainy et al. | 427/2.1 |
| 2004/0047980 A1 | 3/2004 | Pacetti et al. | |
| 2004/0060508 A1 * | 4/2004 | Pacetti et al. | 118/264 |
| 2004/0062853 A1 * | 4/2004 | Pacetti et al. | 427/2.1 |
| 2004/0073298 A1 | 4/2004 | Hossainy | |
| 2004/0093077 A1 * | 5/2004 | White et al. | 623/1.16 |
| 2004/0096504 A1 * | 5/2004 | Michal | 424/471 |
| 2004/0098095 A1 | 5/2004 | Burnside et al. | |
| 2004/0127970 A1 * | 7/2004 | Saunders et al. | 623/1.15 |
| 2004/0143317 A1 | 7/2004 | Stinson et al. | |
| 2004/0191405 A1 * | 9/2004 | Kerrigan | 427/2.24 |
| 2004/0199242 A1 | 10/2004 | Hong et al. | |
| 2004/0213893 A1 | 10/2004 | Boulais | |
| 2004/0232120 A1 * | 11/2004 | Wessner | 219/121.67 |
| 2004/0260386 A1 * | 12/2004 | Shalaby | 623/1.15 |
| 2005/0069630 A1 * | 3/2005 | Fox et al. | 427/2.24 |
| 2005/0107864 A1 * | 5/2005 | Hong et al. | 623/1.15 |
| 2005/0203567 A1 | 9/2005 | Linder et al. | |
| 2005/0230266 A1 | 10/2005 | Callol et al. | |
| 2006/0036311 A1 * | 2/2006 | Nakayama et al. | 623/1.15 |
| 2006/0058866 A1 * | 3/2006 | Cully et al. | 623/1.11 |
| 2006/0135985 A1 | 6/2006 | Cox et al. | 606/194 |
| 2006/0155364 A1 * | 7/2006 | Holloway et al. | 623/1.16 |
| 2006/0276886 A1 | 12/2006 | George et al. | |
| 2006/0287715 A1 * | 12/2006 | Atladottir et al. | 623/1.49 |
| 2007/0032858 A1 * | 2/2007 | Santos et al. | 623/1.16 |
| 2008/0015676 A1 | 1/2008 | Kantor | |
| 2008/0023860 A1 | 1/2008 | Dehennau et al. | 264/7 |
| 2008/0119943 A1 * | 5/2008 | Armstrong et al. | 623/23.7 |
| 2008/0234810 A1 | 9/2008 | Carlson et al. | 623/1.42 |
| 2009/0182404 A1 * | 7/2009 | Shokoohi | 623/1.11 |
| 2009/0319028 A1 * | 12/2009 | Ramzipoor et al. | 623/1.17 |
| 2010/0100171 A1 * | 4/2010 | Atladottir et al. | 623/1.42 |
| 2010/0127427 A1 * | 5/2010 | Kia et al. | 264/313 |
| 2010/0145423 A1 * | 6/2010 | Seifert | 607/116 |

(56) References Cited

U.S. PATENT DOCUMENTS

| | | | |
|---|---|---|---|
| 2011/0048566 A1* | 3/2011 | Theis | 138/124 |
| 2011/0056350 A1* | 3/2011 | Gale et al. | 83/54 |
| 2012/0013061 A1* | 1/2012 | Atladottir et al. | 269/47 |
| 2013/0119586 A1* | 5/2013 | Gale et al. | 264/400 |

* cited by examiner

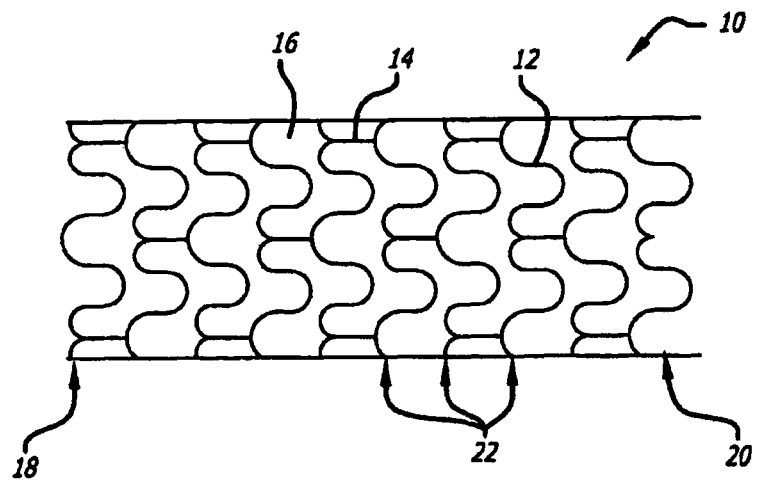
FIG. 9
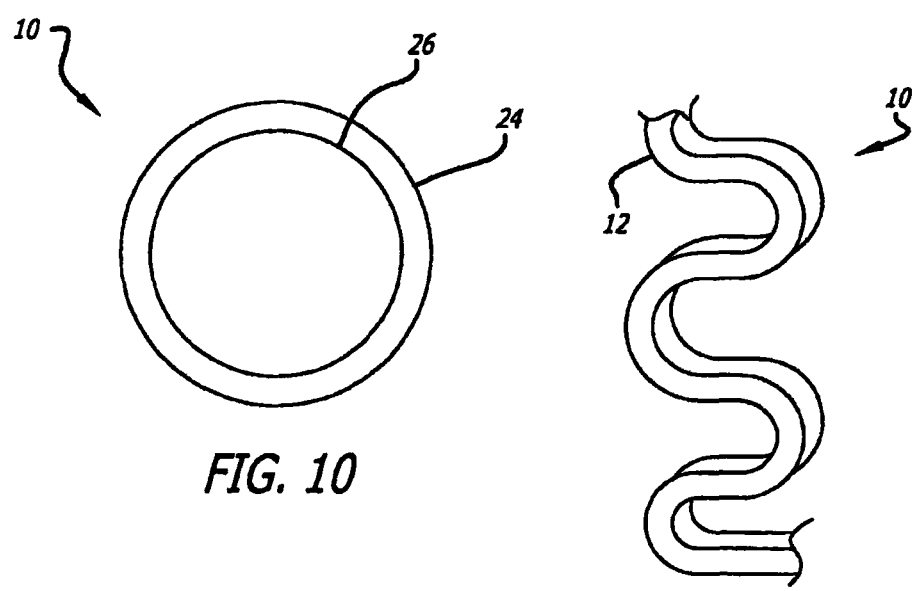
FIG. 10
FIG. 11

ASSEMBLY FOR MAKING A POLYMERIC MEDICAL DEVICE

CROSS-REFERENCE TO RELATED APPLICATIONS

This application is a continuation of U.S. application Ser. No. 12/579,359, filed Oct. 14, 2009, now U.S. Pat. No. 8,066,762, which is a divisional of U.S. application Ser. No. 11/157,145, filed on Jun. 20, 2005, now U.S. Pat. No. 7,622,070, both of which applications are incorporated by reference in their entirety.

BACKGROUND OF THE INVENTION

The invention relates to radially expandable endoprostheses which are adapted to be implanted in a lumen of a tubular organ. An "endoprosthesis", or stent, corresponds to an artificial implantable medical device that is placed inside the body. A "lumen" refers to a cavity of a tubular organ such as a blood vessel. A stent is an example of these endoprostheses. Stents are generally cylindrically shaped devices which function to hold open and sometimes expand a segment of a blood vessel or other anatomical lumens such as urinary tracts and bile ducts. Stents are often used in the treatment of atherosclerotic stenosis in blood vessels. "Stenosis refers to a narrowing or constriction of the diameter of a bodily passage or orifice. In such treatments, stents reinforce vessels and prevent restenosis following angioplasty in the vascular system. "Restenosis" refers to the reoccurrence of stenosis in a blood vessel or heart valve after it has been treated (as by balloon angioplasty or valvuloplasty) with apparent success.

A treatment involving a stent includes both delivery and deployment of the stent. "Delivery" refers to introducing and transporting the stent through a lumen of a tubular organ to a region requiring treatment. "Deployment" corresponds to the expanding of the stent within the lumen at the treatment region. Delivery and deployment of a stent may be accomplished by positioning the stent about one end of a catheter, inserting the end of the catheter through the skin into the lumen, advancing the catheter in the lumen to a desired treatment location, expanding the stent at the treatment location, and then removing the catheter from the lumen. In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn allowing the stent to self-expand.

Stents have been made of many materials including metals and polymers. Polymer materials include both nonbioerodable and bioerodable plastic materials. In some applications, a polymeric bioerodable stent may be more advantageous than a metal stent due to its biodegradeability and increased flexibility relative to the metal stent. The cylindrical structure of a stent is typically composed of a scaffolding that includes a pattern or network of interconnecting structural elements or struts. The scaffolding can be formed from wires, tubes, or planar films of material rolled into a cylindrical shape. In addition, a medicated stent may be fabricated by coating the surface of either a metallic or polymeric scaffolding with a polymeric carrier. The polymeric carrier can include an active agent or drug. Furthermore, the pattern that makes up the stent allows the stent to be radially expandable and longitudinally flexible. Longitudinal flexibility facilitates delivery of the stent and rigidity is needed to hold open a lumen of a tubular organ. Generally, the pattern should be designed to maintain the longitudinal flexibility and rigidity required of the stent. The stent should also have adequate strength in the circumferential direction.

A number of techniques have been suggested for the fabrication of stents from tubes and planar films or sheets. One such technique involves laser cutting or etching a pattern onto a material. Laser cutting may be performed on a planar film of a material which is then rolled into a tube. Alternatively, a desired pattern may be etched directly onto a tube. Other techniques involve cutting a desired pattern into a sheet or a tube via chemical etching or electrical discharge machining Laser cutting of stents has been described in a number of publications including U.S. Pat. No. 5,780,807 to Saunders, U.S. Pat. No. 5,922,005 to Richter and U.S. Pat. No. 5,906,759 to Richter.

In a typical method of manufacturing a metal stent with a laser, a mandrel is placed inside the lumen of metal tubing. A "mandrel" refers to a metal bar or rod on which an implantable medical device may be shaped. The mandrel provides structural support to the tubing as it is being cut and shaped. See, e.g., U.S. Pat. No. 5,780,807 to Saunders.

SUMMARY OF THE INVENTION

Briefly and in general terms, the present invention is directed to an assembly for making a polymeric implantable medical device from a polymer tube. In aspects of the present invention, an assembly comprises a mandrel made of a first bioabsorbable polymer; and a tube made of a second bioabsorbable polymer, the tube disposed over the mandrel, the mandrel passing through the tube. In other aspects of the present invention assembly comprises a mandrel having an outer surface made of a first bioabsorbable polymer; and a tube made of a second bioabsorbable polymer, the tube removably disposed over the mandrel.

The features and advantages of the invention will be more readily understood from the following detailed description which should be read in conjunction with the accompanying drawings.

BRIEF DESCRIPTION OF THE DRAWINGS

FIG. 9 shows an enlarged view of a polymeric stent manufactured by the stent manufacturing device of FIG. 5.

FIG. 10 is a cross-sectional view of the polymeric stent of FIG. 9.

FIG. 11 is an enlarged view of a portion of a distal ring of the polymeric stent of FIG. 9.

DETAILED DESCRIPTION OF PREFERRED EMBODIMENTS OF THE INVENTION

A polymeric stent may be manufactured by a variety of methods. In one method, the polymeric stent may be formed by laser cutting a flat polymeric sheet in the form of rings and links, and then subsequently rolling the pattern into the shape of the cylindrical stent and providing a longitudinal weld to form the stent. In another method, a flat polymeric sheet may be chemically etched and then subsequently rolled and welded to form the polymeric stent. Additionally, a polymeric wire may be coiled to form a polymeric stent. In yet another method, a polymeric stent may be formed from a tube by laser cutting a pattern of cylindrical rings and connecting rings in the tube itself. See, e.g., U.S. Pat. No. 6,585,755 to Jackson et al.

In a conventional lasing process of manufacturing a polymeric stent from a tube, a mandrel may not typically be employed. Due to the retentive nature of polymeric materials for foreign particulates, a glass or metal mandrel may contaminate the polymeric stent if a laser beam from the laser strikes it and releases such contaminates. In other words, a glass mandrel may leave glass particulates, and a metal mandrel may leave large amounts of metal oxide contamination melted into the inner surface of the polymer stent, respectively. Such contaminants may cause adverse effects during and/or after the stent is implanted into the lumen of a bodily organ.

Non-use of a mandrel in the manufacturing process of a polymeric stent, however, may cause problems aside from contamination through use of glass or metal mandrels. It has been observed that in the manufacture of polymeric stents, damage to the inner surface of the stent can occur. The damage is typically in the form of at least one angled cut, or "nick", within the inner surface area. The angled cuts are the result of the laser beam reaching the inner surface as the equal-but-opposite outer surface is being lased. The damage caused thereby may cause problems with delivery of the stent and/or adverse body reactions. This problem may be remedied by use of a typical mandrel (which may provide a shielding effect) in the manufacturing process; however, the problems associated with the use of metal or glass mandrels as described previously may result.

Figure 1:
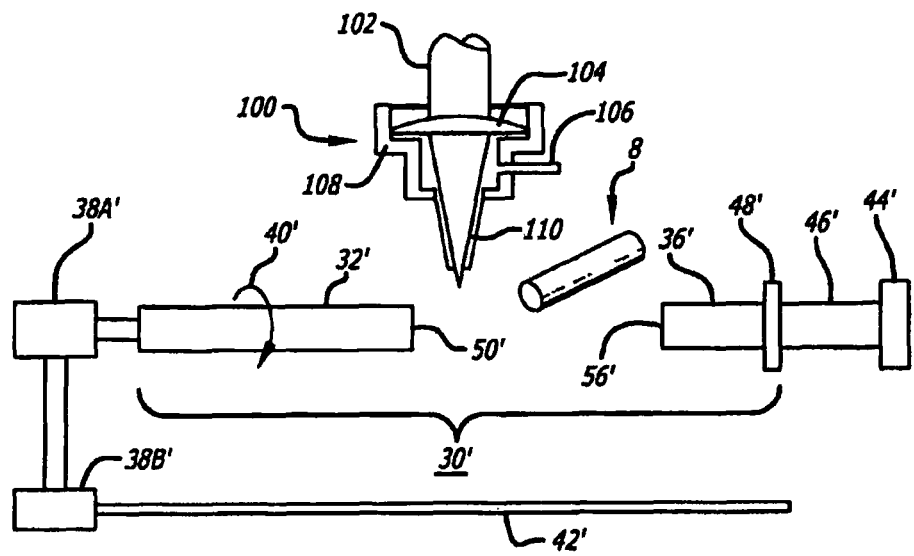
FIG. 1 illustrates a polymeric stent manufacturing device used in one form of a method for manufacturing a polymeric stent pursuant to the present invention.

FIG. 1 illustrates an embodiment of a polymeric stent manufacturing device 30' related to the manufacturing process of a polymeric stent. Device 30' for supporting a stent 10' (not shown in FIG. 1) includes a support member 32' and a lock member 36'. Support member 32' may connect to a motor 38A' to provide rotational motion about the longitudinal axis of a stent (depicted by arrow 40'). Another motor 38B' may also be provided for moving device 30' in a back and forth linear direction along rail 42'. Polymeric stent manufacturing device 30' may be in fluid communication with a vacuum device 44' for collecting excess polymeric material. Lock member 36' may be coupled to the vacuum device 44' via a conduit 46'. A coupler 48' allows device 30' to rotate with respect to conduit 46' and vacuum 44'. In some embodiments, "device" 44' can be a temperature adjuster for adjusting the temperature of the tube 8 to a temperature other than room temperature before, during and/or after the etching process.

Figure 2:
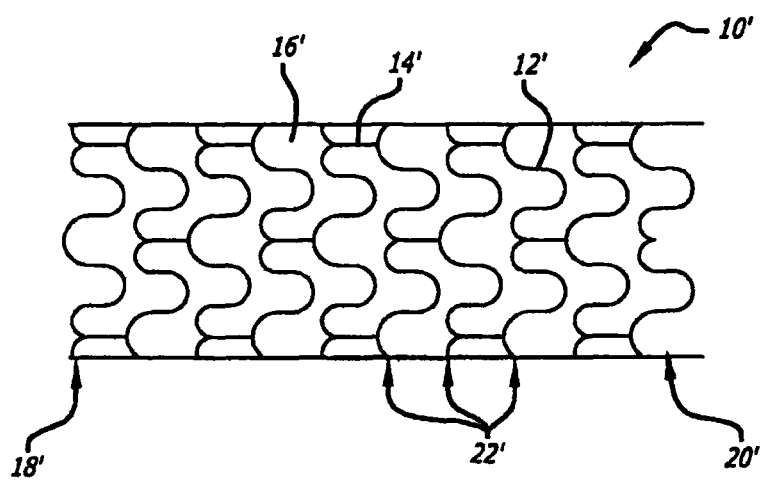
FIG. 2 shows an enlarged view of a polymeric stent manufactured by the stent manufacturing device of FIG. 1.

In the manufacturing process, a polymeric tube 8 may be mounted between support member 32' and lock member 36'. The wall thickness of the polymeric tube 8 will typically vary throughout the tube body due to variations in the manufacturing process of polymeric tubes. A coaxial gas jet, rotary collet, tube support and beaming block apparatus of a laser (from hereonout abbreviated as a laser 100) may then be used for the etching process to form a polymeric stent 10' from the polymeric tube 8. The laser 100 can include a laser beam 102, a focusing lens 104, a gas input 106, a coaxial gas jet assay 108 and a gas jet 110. A resultant polymeric stent 10' manufactured using device 30' is illustrated in FIG. 2. Polymeric stent 10' includes a plurality of struts 12' linked by connecting elements 14' with gaps 16' positioned in between struts 12' and connecting elements 14'. The polymeric stent 10' can include a proximal ring 18', a distal ring 20' and at least one central ring 22'.

Figure 3:
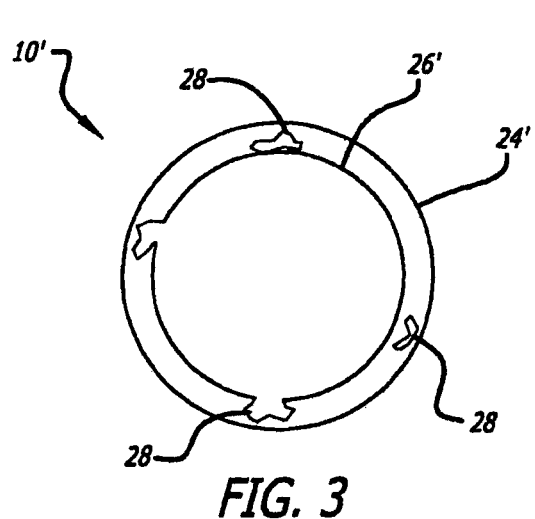
FIG. 3 is a cross-sectional view of the polymeric stent of FIG. 2.
Figure 4:
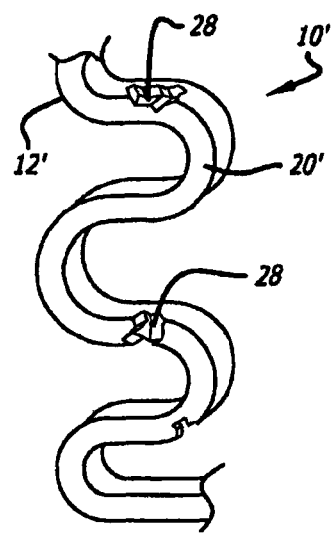
FIG. 4 is an enlarged view of a portion of a distal ring of the polymeric stent of FIG. 2.

FIG. 3 is a cross-section of the polymeric stent 10' of FIG. 2. As shown, the stent 10' includes an inner surface 26' and an outer surface 24'. The inner surface 26' of the stent 10' may have at least one "nick" or angled cut 28 when manufactured using the device 30' as discussed in connection with FIG. 1. In FIG. 4, an enlarged view of a portion of the distal ring 20' is depicted. In this view, at least one angled cut 28 on the inner surface 26' can be seen more clearly. It should be understood that the angled cuts 28 may occur throughout the inner surface 26' of the stent 10'.

The manufacturing process as discussed in connection with FIG. 1 may lead to the manifestation of angled cuts 28. For example, a shielding effect to the inner surface of a polymeric tube that would otherwise be provided by a mandrel during the manufacturing process of a polymeric stent contributes to the manifestation of angled cuts 28. In addition, the inherent varying wall thickness of the polymeric tubes may contribute to the manifestation of angled cuts 28. As an illustration, the power of the laser 100 may be adjusted to etch a first portion of the polymeric tube 8 with a first thickness. However, this same power may be too strong for the etching of a second portion of polymeric tube 8 with a second thickness. As a result, although appropriate for the first portion of polymeric tube 8 with the first thickness, the same power of the laser 100 for the second portion of the polymer tube 8 with the second thickness may be too strong and therefore cause the manifestation of angled cuts 28. Consequently, the yield of viable polymeric stents using the method and device as discussed above will typically be in the range of 30% to 90%.

Figure 5:
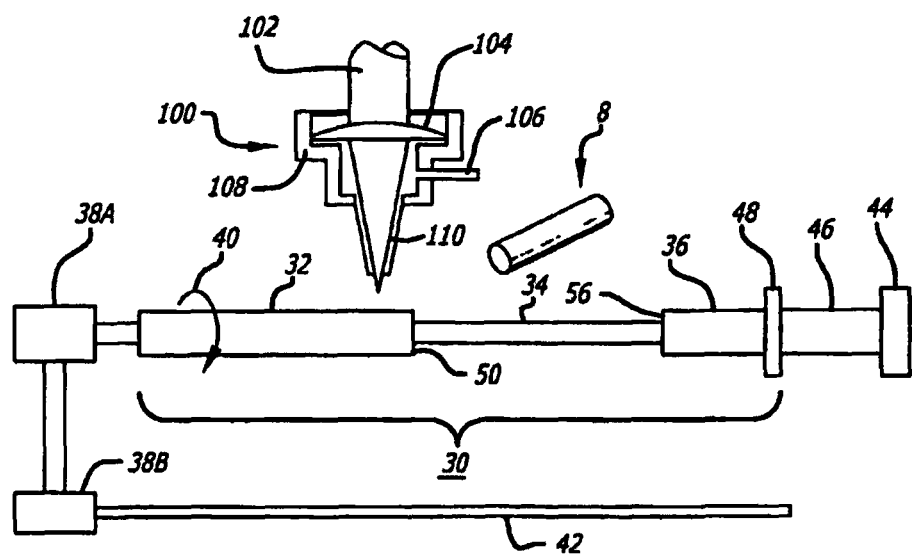
FIG. 5 illustrates an alternative embodiment of a polymeric stent manufacturing device used in one form of a method pursuant to the present invention.
Figure 6:
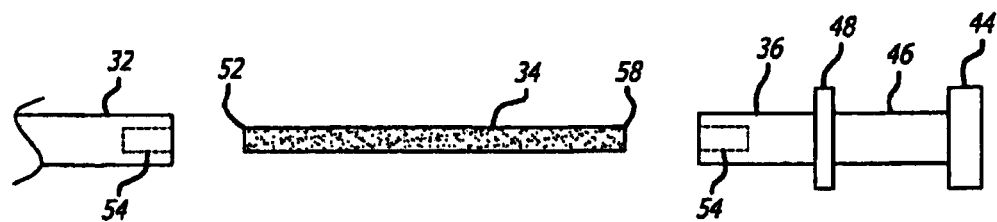
FIG. 6 is an exploded view of the alternative embodiment of the device in FIG. 5.

In FIGS. 5 and 6, an embodiment of a polymeric stent manufacturing device 30 related to a manufacturing process of the present invention is illustrated. Device 30 for supporting a stent 10 (not shown in this figure) can include a support member 32, a polymeric mandrel 34 and a lock member 36. A polymeric mandrel is a mandrel made wholly or in part from at least one type of polymer of a combination of polymers, such as in a blended chemically bonded or grafted form. The polymeric mandrel can also be a mandrel that is coated with at least one type of polymer or a combination of polymers. Support member 32 may connect to a motor 38A to provide rotational motion about the longitudinal axis of a stent (depicted by arrow 40). Another motor 38B may also be provided for moving device 30 in a back-and-forth linear direction along rail 42. The types and specifications of the various motors which can be used in any of the embodiments herein would be apparent to those skilled in the art. The term stent is broadly intended to include self- and balloon-type as well stent-grafts. Polymeric stent manufacturing device 30 can be in fluid communication with a vacuum device 44 for collecting excess material that may discharge off of the mandrel 34 or the stent 10. In addition, lock member 36 is coupled to vacuum device 44 via a conduit 46. A coupler 48 allows device 30 to rotate with respect to conduit 46 and vacuum 44. In some embodiments, "device" 44 can be a temperature adjuster for adjusting the temperature of the tube 8 to a temperature other than room temperature before, during and/or after the etching process.

Support member 32 includes a flat end 50 that is coupled to a first end 52 of mandrel 34. In accordance to one embodiment, mandrel 34 can be permanently affixed to support member 32. Alternatively, support member 32 can include a bore 54 for receiving first end 52 of mandrel 34. First end 52 of mandrel 34 can be threaded to screw into bore 54. Alternatively, a non-threaded first end 52 of mandrel 34 can be press-fitted or friction-fitted within bore 54. Bore 54 should be deep enough so as to allow mandrel 34 to securely mate with support member 32. The depth of bore 54 can be over-extended so as to allow a significant length of mandrel 34 to penetrate the bore. This would allow the length of mandrel 34 to be adjusted to accommodate stents of various sizes.

Lock member 36 can include a flat end 56 that can be permanently affixed to a second end 58 of mandrel 34 if end 52 of mandrel 34 is disengagable from support member 32. A bore 54 extends along lock member 36 for allowing mandrel 34 to be in fluid communication with vacuum device 44. In accordance with another embodiment, mandrel 34 can have a threaded second end 58 for screwing into bore 54. A non-threaded second end 58 and bore 54 combination can also be employed such that second end 58 of mandrel 34 is press-fitted or friction-fitted within bore 54. Lock member 36 can be incrementally moved closer to support member 32. Accordingly, stents of any length can be securely pinched between flat ends 50 and 56 of the support and lock members 32 and 36. A stent need not, however, be pinched between ends 50 and 56; a stent can be simply crimped tightly on mandrel 34.

Figures 7A, 7B:
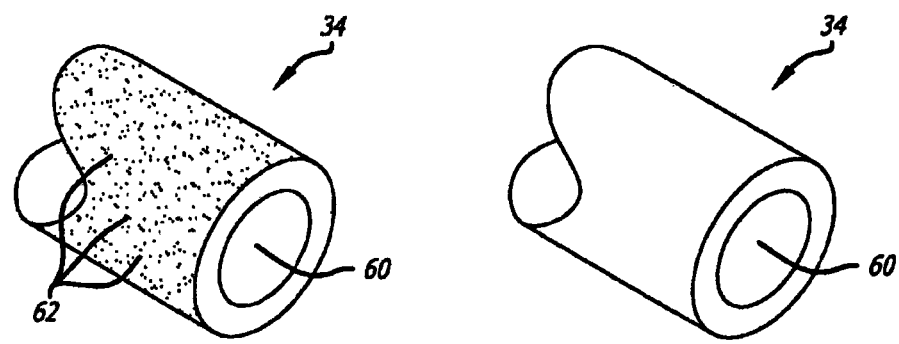
FIG. 7A illustrates an embodiment of a polymeric mandrel of the present invention and used in one form of a method of the present invention.
FIG. 7B illustrates an alternative embodiment of a polymeric mandrel of the present invention and used in one form of a method of the present invention.

An embodiment of a portion of polymeric mandrel 34 is illustrated in FIG. 7A and includes a hollow tubular body having a mandrel bore 60 extending through the body of mandrel 34. In addition, mandrel 34 may have pores 62 on its surface that are in communication with mandrel bore 60. In other words, pores 62 penetrate all the way through the body of mandrel 34. Mandrel bore 60 and pores 62 can be of any suitable size and the number of pores 62 can be selected for effectively allowing excess material to be vacuumed off of the stent and mandrel 34. However, the pores 62 should not cause manufacturing defects. In some embodiments, the vacuum device 34 should be able to apply positive pressure so as to blow out air or a gas (such as an inert gas, for example, argon) in or out from the mandrel 34. The blowing or vacuuming can be conducted during or after the laser etching. In an alternative embodiment, the mandrel 34 may be solid (see FIG. 7B).

Polymeric mandrel 34 can be made from or coated with a biostable polymer or a bioerodable, biodegradable or bioabsorbable polymer. Bioerodable, biodegradable or bioabsorbable are intended to be used interchangeably unless otherwise indicated. In some embodiments, the polymer is the same as a polymer used to make the implantable medical device or stent 10. In some embodiments, the polymer can be different, so long as the polymer is biocompatible. If a combination of polymers is used from the device or mandrel 34, at least one of the polymers can be the same.

Representative examples of biocompatible polymers that can be used for mandrel 34 include, but are not limited to, fluorinated polymers or copolymers such as poly(vinylidene fluoride), poly(vinylidene fluoride-co-hexafluoro propene), poly(tetrafluoroethylene), and expanded poly(tetrafluoroethylene); poly(sulfone); poly(Nvinyl pyrrolidone); poly(aminocarbonates); poly(iminocarbonates); poly(anhydridecoimides), poly(hydroxyvalerate); poly(L-lactic acid); poly (L-lactide); poly(caprolactones); poly(lactide-co-glycolide); poly(hydroxybutyrates); poly(hydroxybutyrate-co-valerate); poly(dioxanones); poly(orthoesters); poly(anhydrides); poly (glycolic acid); poly(glycolide); poly(D,L-lactic acid); poly (D,L-lactide); poly(glycolic acid-co-trimethylene carbonate); poly(phosphoesters); poly(phosphoester urethane); poly (trimethylene carbonate); poly(iminocarbonate); poly (ethylene); and any derivatives, analogs, homologues, congeners, salts, copolymers and combinations thereof.

In some embodiments, the polymers include, but are not limited to, poly(propylene) co-poly(ether-esters) such as, for example, poly(dioxanone) and poly(ethylene oxide)/poly (lactic acid); poly(anhydrides), poly(alkylene oxalates); poly (phosphazenes); poly(urethanes); silicones; poly(esters; poly (olefins); copolymers of poly(isobutylene); copolymers of ethylene-alphaolefin; vinyl halide polymers and copolymers such as poly(vinyl chloride); poly(vinyl ethers) such as, for example, poly(vinyl methyl ether); poly(vinylidene halides) such as, for example, poly(vinylidene chloride); poly(acrylonitrile); poly(vinyl ketones); poly(vinyl aromatics) such as poly(styrene); poly(vinyl esters) such as poly(vinyl acetate); copolymers of vinyl monomers and olefins such as poly(ethylene-co-vinyl alcohol) (EVAL), copolymers of acrylonitrile-styrene, ABS resins, and copolymers of ethylene-vinyl acetate; and any derivatives, analogs, homologues, congeners, salts, copolymers and combinations thereof.

In some embodiments, the polymers include, but are not limited to, poly(amides) such as Nylon 66 and poly(caprolactam); alkyd resins; poly(carbonates); poly(oxymethylenes); poly(imides); poly(ester amides); poly(ethers) including poly(alkylene glycols) such as, for example, poly (ethylene glycol) and poly(propylene glycol); epoxy resins; polyurethanes; rayon; rayon-triacetate; biomolecules such as, for example, fibrin, fibrinogen, starch, poly(amino acids); peptides, proteins, gelatin, chondroitin sulfate, dermatan sulfate (a copolymer of D-glucuronic acid or L-iduronic acid and N-acetyl-D-galactosamine), collagen, hyaluronic acid, and glycosaminoglycans; other polysaccharides such as, for example, poly(N-acetylglucosamine), chitin, chitosan, cellulose, cellulose acetate, cellulose butyrate, cellulose acetate butyrate, cellophane, cellulose nitrate, cellulose propionate, cellulose ethers, and carboxymethylcellulose; and any derivatives, analogs, homologues, congeners, salts, copolymers and combinations thereof.

In some embodiments, at least one of polymers can be a poly(ester amide), a poly(lactide) or a poly(lactide-co-glycolide) copolymer; and any derivatives, analogs, homologues, congeners, salts, copolymers and combinations thereof.

In some embodiments, the polymers can be biodegradable, bioerodable and/or bioabsorbable. Examples of biodegradable polymers include, but are not limited to, polymers having repeating units such as, for example, an a-hydroxycarboxylic acid, a cyclic diester of an a-hydroxycarboxylic acid, a dioxanone, a lactone, a cyclic carbonate, a cyclic oxalate, an epoxide, a glycol, an anhydride, a lactic acid, a glycolic acid, a lactide, a glycolide, an ethylene oxide, an ethylene glycol, and any derivatives, analogs, homologues, congeners, salts, copolymers and combinations thereof.

In some embodiments, the biodegradable polymers include, but are not limited to, polyesters, poly(ester amides); poly(hydroxyalkanoates) (PHA), amino acids; PEG and/or alcohol groups; polycaprolactones, poly(D-lactide), poly(L-lactide), poly(D,L-lactide), poly(meso-lactide), poly(L-lactide-co-meso-lactide), poly(D-lactide-comeso-lactide), poly (D,L-lactide-co-meso-lactide), poly(D,L-lactide-co-PEG) block copolymers, poly(D,L-lactide-co-trimethylene carbonate), polyglycolides, poly(lactide-coglycolide), polydioxanones, polyorthoesters, polyanhydrides, poly(glycolic acid-cotrimethylene carbonate), polyphosphoesters, polyphosphoester urethanes, poly(amino acids), polycyanoacrylates, poly(trimethylene carbonate), poly(imino carbonate), polycarbonates, polyurethanes, copoly(ether-esters) (e.g. PEO/PLA), polyalkylene oxalates, polyphosphazenes, PHA-PEG, and any derivatives, analogs, homologues, salts, copolymers and combinations thereof.

In other embodiments, the polymers can be poly(glycerol sebacate); tyrosine-derived polycarbonates containing desaminotyrosyl-tyrosine alkyl esters such as, for example, desaminotyrosyl-tyrosine ethyl ester (poly(DTE carbonate)); and any derivatives, analogs, homologues, salts, copolymers and combinations thereof.

In some embodiments, the polymers are selected such that they specifically exclude any one or any combination of any of the polymers taught herein.

Figure 8:
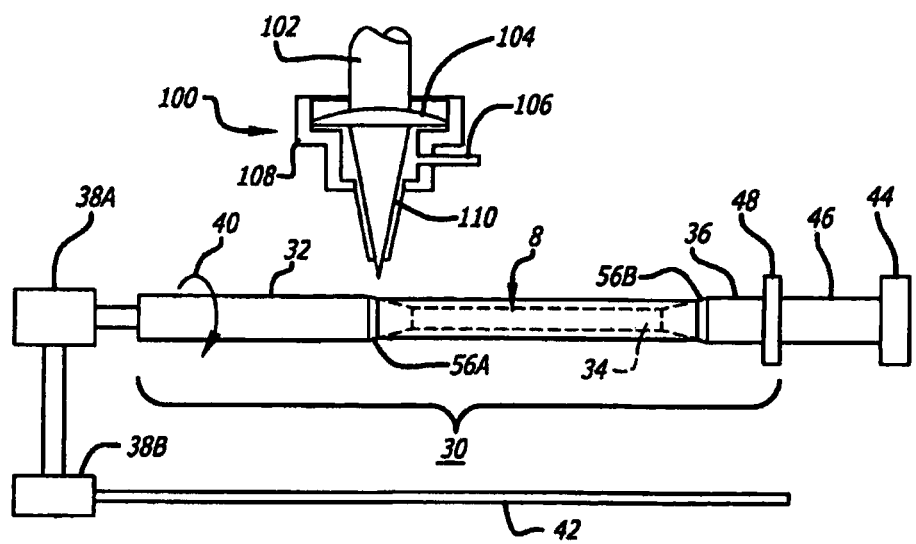
FIG. 8 illustrates a second alternative embodiment of a polymeric stent manufacturing device used in one form of a method pursuant to the present invention.

FIG. 8 illustrates a view of polymeric stent mandrel device 30 according to another embodiment of the invention. Support member 32 and lock member 36 include conical end portions 56A and 56B, instead of flat ends, for penetrating into ends of stent 10. The end portions 56A and 56B can taper inwardly at an angle $0_1$ of about 15° to about 75°, more narrowly from about 30° to about 60°. By way of example, angle 0, can be about 45°. The outer surface of mandrel 34 will typically be smaller than the inner surface of stent 10, as positioned on fixture 30, so as to prevent the outer surface of mandrel 34 from making contact with the inner surface of stent 10.

In the manufacturing process using device 30, a polymeric tube 8 may be placed on the polymeric mandrel 34 between support member 32 and lock member 36. The polymeric tube 8 may typically be between twelve to two-hundred millimeters long depending on its intended therapeutic application. Additionally, the inner and outer surfaces of the polymeric tube 8 may vary in accordance with the intended therapeutic application and in correspondence with the outer surface of the mandrel 34. In some embodiments, the OD of the polymeric tube 8 may approximately be equivalent to the ID of the mandrel 34. In other embodiments, the OD of the polymeric tube 8 may be smaller than the ID of the mandrel 34. For example, for a polymeric tube 8 of size 0.084"OD and 0.070"ID, a corresponding polymer mandrel in the range of 0.025" OD to 0.035" OD may be used. Generally, mandrels may range in size from 0.010" OD to 0.050" OD, typically supplied in the sizes 0.014" OD or 0.035" OD.

A laser 100 may then be used for the etching process to form a polymeric stent 10 from polymeric tube 8. The laser 100 may be used in a range of fifty milliwatts to one watt, depending on the environmental conditions surrounding the laser. In contrast to the method employing device 30', the method employing device 30 with polymeric mandrel 34 reduces the need to tailor the power from the laser 100 to the wall thickness of the polymer tube 8, thus reducing the time it takes to cut the stent 10. A typical lasing process takes approximately two minutes to twelve minutes, more particularly approximately six minutes, pursuant to a method of this invention.

In FIG. 9, a polymeric stent 10 manufactured in accordance with device 30 is illustrated. As discussed previously, the polymeric stent 10 can include a plurality of struts 12 linked by connecting elements 14, with gaps 16 positioned between the struts and the connecting elements. The polymeric stent 10 can also include a proximal ring 18, a distal ring 20 and at least one central ring 22. Generally, the polymeric stent 10 is a bioerodable, biodegradable or bioabsorbable implantable medical device that is intended to remain in the body until its intended function is achieved.

In FIGS. 10 and 11, cross-sectional and enlarged views of the polymer stent of FIG. 9 are illustrated, respectively. Generally absent from the inner surface 26 is at least one angled cut 28. This is substantially due to the mandrel 34, which provides a shielding effect to the inner surface 26 when the equal-but-opposite outer surface 24 is being lased during the manufacturing process. Moreover, because the mandrel 34 is comprised of a biocompatible polymer, the problems of undesirable residual contaminants left by typical glass or metal mandrels, for example, are substantially reduced or completely eliminated. Finally, using the method related to device 30, slight wall thickness variations of the polymeric tube 8 can be tolerated to a greater extent due to the shielding effect of the polymeric mandrel 34 as discussed previously. Overall, a higher yield of usable commercially polymeric stents may be produced using the method employing device 30 with polymeric mandrel 34. It is anticipated that the yield of polymeric stents using the method and device as just described will approach 100%.

The polymeric stent 10 described in FIGS. 9, 10 and 11 may be coated with one or more therapeutic agents, including an anti-proliferative, anti-inflammatory or immune modulating, anti-migratory, anti-thrombotic or other pro-healing agent or a combination thereof. The anti-proliferative agent can be a natural proteineous agent such as a cytotoxin or a synthetic molecule or other substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin 11, actinomycin X1, and actinomycin C1), all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-0-(3-hydroxy)propyl-rapamycin, 40-0-[2-(2-hydroxy)ethoxy]ethyl-rapamycin, or 40-0-tetrazole-rapamycin, 40-epi-(N1-tetrazolyl)-rapamycin (ABT-578 manufactured by Abbot Laboratories, Abbot Park, Ill.), prodrugs thereof, co-drugs thereof, and combinations thereof.

The anti-inflammatory agent can be a steroidal anti-inflammatory agent, a nonsteroidal anti-inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

These agents can also have anti-proliferative and/or anti-inflammmatory properties or can have other properties such as antineoplastic, antiplatelet, anticoagulant, anti-fibrin, anti-thrombonic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax a (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiasterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl(4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzidee from Merck & Co., Inc., Whitehouse Station, N.J.). An example of an antiallergic agent is permirolast potassium. Other therapeutic substances or agents which may be appropriate include alpha-interferon, and genetically engineered epithelial cells. The foregoing substances are listed by way of example and are not meant to be limiting. Other active agents which are currently available or that may be developed in the future are equally applicable.

The coating method may be applied by a variety of methods, such as those disclosed in U.S. Pat. No. 6,818,063 to Kerrigan and U.S. Pat. No. 6,695,920 to Pacetti et al. In addition, the therapeutic drug may be incorporated within the polymeric tube 8 thereof, such as disclosed in U.S. Pat. No. 5,605,696 to Eury et al. Also, the polymeric tube 8 may include at least two layers of polymers with different chemical characteristics for purposes of, for example, adjusting the flexibility characteristic of the polymeric stent 10.

From the foregoing detailed description, it will be evident that there are a number of changes, adaptations and modifications of the present invention which come within the province of those skilled in the art. The scope of the invention includes any combination of the elements from the different species or embodiments disclosed herein, as well as subassemblies, assemblies, and methods thereof. However, it is intended that all such variations not departing from the spirit of the invention be considered as within the scope thereof.

What is claimed is:

1. An assembly for making a polymeric implantable medical device from a polymer tube, the assembly comprising:
   a mandrel made of a first bioabsorbable polymer; and
   a tube made of a second bioabsorbable polymer, the tube disposed over the mandrel, the mandrel passing through the tube, the tube arranged to be cut to make an implantable medical device with the mandrel disposed within the implantable medical device, and the mandrel is configured for removal from within the implantable medical device prior to implantation of the implantable medical device.

2. The assembly of claim 1, further comprising a laser arranged and configured to cut the tube while the tube is disposed over the mandrel, and at least one motor configured to move the mandrel relative to the laser while the tube is disposed over the mandrel.

3. The assembly of claim 1, wherein the first bioabsorbable polymer and the second bioabsorbable polymer have the same composition, and wherein the first bioabsorbable polymer and the second bioabsorbable polymer are a material selected from the group consisting of poly(lactide), poly(lactide-co-glycolide) copolymer, and poly(L-lactide).

4. The assembly of claim 1, wherein the first bioabsorbable polymer and the second bioabsorbable polymer comprise poly(L-lactide).

5. The assembly of claim 1, wherein the mandrel includes a tubular body, a mandrel bore that extends through the tubular body, and a plurality of pores extending from the mandrel bore to an outer surface of the mandrel.

6. The assembly of claim 5, further comprising a pressure device coupled to the mandrel bore, the pressure device configured to apply positive or negative pressure to the mandrel bore.

7. The assembly of claim 6, further comprising a laser, a motor configured to rotate the tubular body of the mandrel relative to the laser, and a coupler disposed between the mandrel bore and the pressure device, the coupler configured to allow rotation of the tubular body relative to the pressure device.

8. The assembly of claim 1, wherein an outer surface of the mandrel does not contact an inner surface of the tube.

9. The assembly of claim 1, wherein the mandrel has an outer diameter smaller than an inner diameter of the tube.

10. The assembly of claim 1, wherein the mandrel is affixed to a support member configured to support an end of the tube while the tube is being cut.

11. An assembly for making a polymeric implantable medical device from a polymer tube, the assembly comprising:
    a mandrel having an outer surface made of a first bioabsorbable polymer; and
    a tube made of a second bioabsorbable polymer, the tube removably disposed over the mandrel,
    wherein the tube is arranged to be cut to make an implantable medical device with the mandrel disposed within the implantable medical device, and the mandrel is configured for removal from within the implantable medical device prior to implantation of the implantable medical device.

12. The assembly of claim 11, further comprising a laser arranged and configured to cut through the tube and into the mandrel while the tube is disposed over the mandrel, and at least one motor configured to move the mandrel relative to the laser while the tube is disposed over the mandrel.

13. The assembly of claim 11, wherein the first bioabsorbable polymer and the second bioabsorbable polymer have the same composition, and the first bioabsorbable polymer and the second bioabsorbable polymer are a material selected from the group consisting of poly(lactide), poly(lactide-co-glycolide) copolymer, and poly(L-lactide).

14. The assembly of claim 11, wherein the first bioabsorbable polymer and the second bioabsorbable polymer comprise poly(L-lactide).

15. The assembly of claim 11, wherein the mandrel includes a tubular body, a mandrel bore that extends through the tubular body, and a plurality of pores extending from the mandrel bore to the outer surface of the mandrel.

16. The assembly of claim 15, further comprising a pressure device coupled to the mandrel bore, the pressure device configured to apply positive or negative pressure to the mandrel bore.

17. The assembly of claim 16, further comprising a laser, a motor configured to rotate the tubular body of the mandrel relative to the laser, and a coupler disposed between the mandrel bore and the pressure device, the coupler configured to allow rotation of the tubular body relative to the pressure device.

18. The assembly of claim 11, wherein the outer surface of the mandrel does not contact an inner surface of the tube.

19. The assembly of claim 11, wherein the mandrel has an outer diameter smaller than an inner diameter of the tube.

20. The assembly of claim 11, wherein the mandrel is affixed to a support member configured to support an end of the tube.

* * * * *